(12) United States Patent
Bonnette et al.

(10) Patent No.: US 8,974,418 B2
(45) Date of Patent: Mar. 10, 2015

(54) FORWARDLY DIRECTED FLUID JET CROSSING CATHETER

(75) Inventors: Michael J. Bonnette, Minneapolis, MN (US); David B. Morris, Anoka, MN (US); Eric J. Thor, Arden Hills, MN (US)

(73) Assignee: Boston Scientific Limited, Hamilton (BM)

( * ) Notice: Subject to any disclaimer, the term of this patent is extended or adjusted under 35 U.S.C. 154(b) by 1500 days.

(21) Appl. No.: 12/009,807

(22) Filed: Jan. 22, 2008

(65) Prior Publication Data

US 2008/0312672 A1 Dec. 18, 2008

Related U.S. Application Data

(60) Provisional application No. 60/934,284, filed on Jun. 12, 2007.

(51) Int. Cl.
*A61M 5/178* (2006.01)
*A61B 17/3203* (2006.01)

(52) U.S. Cl.
CPC .............................. *A61B 17/32037* (2013.01)
USPC .................................................. 604/164.13

(58) Field of Classification Search
USPC ................. 604/22, 164.01, 164.02, 264, 284, 604/164.13, 528; 606/159
See application file for complete search history.

(56) References Cited

U.S. PATENT DOCUMENTS

| 1,902,418 A | 3/1933 | Pilgrim |
| 3,752,617 A | 8/1973 | Burlis et al. |
| 3,930,505 A | 1/1976 | Wallach |
| 4,168,709 A | 9/1979 | Bentov |

(Continued)

FOREIGN PATENT DOCUMENTS

| DE | 3705339 | 9/1988 |
| DE | 3421390 | 6/1994 |

(Continued)

OTHER PUBLICATIONS

International Preliminary Report on Patentability and Written Opinion from corresponding PCT Publication No. WO2008/154242, dated Oct. 2, 2008.

(Continued)

*Primary Examiner* — Kami A Bosworth
*Assistant Examiner* — Imani Hayman
(74) *Attorney, Agent, or Firm* — Seager, Tufte & Wickhem, LLC

(57) ABSTRACT

A forwardly directed fluid jet crossing catheter having a distally directed cylindrical flow fluid jet stream to cross a chronic total occlusion is set forth. The distal end of the device includes a formable catheter tip region having flexible internal components. Low and high pressure cavities are formed substantially by joined proximal and distal catheter tubes having an adhesive plug seal in common therebetween which partially defines one end of each of the low pressure and high pressure cavities. A guidewire tube and a high pressure tube are aligned along and within the low pressure and high pressure cavities and through the adhesive plug seal. The high pressure tube openly terminates in the high pressure cavity, whereby pressurized fluid transfers from the high pressure cavity in the guidewire tube entry hole to subsequently pass along the guidewire lumen and co-located guidewire to exit as a cylindrical fluid jet stream.

21 Claims, 12 Drawing Sheets

(56) References Cited

U.S. PATENT DOCUMENTS

| | | | |
|---|---|---|---|
| 4,224,943 A | 9/1980 | Johnson et al. | |
| 4,248,234 A | 2/1981 | Assenza et al. | |
| 4,290,428 A | 9/1981 | Durand et al. | |
| 4,328,811 A | 5/1982 | Fogarty | |
| 4,385,635 A | 5/1983 | Ruiz | |
| 4,631,052 A | 12/1986 | Kensey | |
| 4,636,346 A | 1/1987 | Gold et al. | |
| 4,690,672 A | 9/1987 | Veltrup | |
| 4,739,768 A | 4/1988 | Engelson | |
| 4,747,405 A | 5/1988 | Leckrone | |
| 4,781,186 A | 11/1988 | Simpson et al. | |
| 4,782,834 A | 11/1988 | Maguire et al. | |
| 4,790,813 A | 12/1988 | Kensey | |
| 4,842,579 A | 6/1989 | Shiber | |
| 4,883,459 A | 11/1989 | Calderon | |
| 4,888,146 A | 12/1989 | Dandeneau | |
| 4,898,574 A | 2/1990 | Uchiyama et al. | |
| 4,898,591 A | 2/1990 | Jang et al. | |
| 4,902,276 A | 2/1990 | Zakko | |
| 4,913,698 A | 4/1990 | Ito et al. | |
| 4,950,238 A | 8/1990 | Sullivan | |
| 5,011,469 A | 4/1991 | Buckberg et al. | |
| 5,085,649 A | 2/1992 | Flynn | |
| 5,086,842 A | 2/1992 | Cholet | |
| 5,092,873 A | 3/1992 | Simpson et al. | |
| 5,114,399 A | 5/1992 | Kovalcheck | |
| 5,135,482 A | 8/1992 | Neracher | |
| 5,163,431 A | 11/1992 | Griep | |
| 5,215,614 A | 6/1993 | Wijkamp et al. | |
| 5,221,270 A | 6/1993 | Parker | |
| 5,234,416 A | 8/1993 | Macaulay et al. | |
| 5,250,059 A | 10/1993 | Andreas et al. | |
| 5,254,107 A | 10/1993 | Soltesz | |
| 5,259,842 A | 11/1993 | Plechinger et al. | |
| 5,273,526 A | 12/1993 | Dance et al. | |
| 5,300,022 A | 4/1994 | Klapper et al. | |
| 5,308,342 A | 5/1994 | Sepetka et al. | |
| 5,318,518 A | 6/1994 | Plechinger et al. | |
| 5,320,599 A | 6/1994 | Griep et al. | |
| 5,324,285 A | 6/1994 | Cannon | |
| 5,342,386 A | 8/1994 | Trotta | |
| 5,356,388 A | 10/1994 | Sepetka et al. | |
| 5,358,485 A | 10/1994 | Vance et al. | |
| 5,370,609 A | 12/1994 | Drasler et al. | |
| 5,372,601 A | 12/1994 | Lary | |
| 5,380,307 A | 1/1995 | Chee et al. | |
| 5,399,164 A | 3/1995 | Snoke et al. | |
| 5,425,723 A | 6/1995 | Wang | |
| 5,456,674 A | 10/1995 | Bos et al. | |
| 5,478,330 A | 12/1995 | Imran et al. | |
| 5,492,532 A * | 2/1996 | Ryan et al. | 604/103.09 |
| 5,496,267 A | 3/1996 | Drasler et al. | |
| 5,496,294 A | 3/1996 | Hergenrother et al. | |
| 5,499,973 A | 3/1996 | Saab | |
| 5,531,685 A | 7/1996 | Hemmer et al. | |
| 5,542,924 A | 8/1996 | Snoke et al. | |
| 5,554,121 A | 9/1996 | Ainsworth et al. | |
| 5,571,094 A | 11/1996 | Sirhan | |
| 5,599,325 A | 2/1997 | Ju et al. | |
| 5,624,397 A | 4/1997 | Snoke et al. | |
| 5,634,897 A | 6/1997 | Dance et al. | |
| 5,658,263 A | 8/1997 | Dang et al. | |
| 5,662,622 A | 9/1997 | Gore et al. | |
| 5,676,659 A | 10/1997 | McGurk | |
| 5,681,336 A | 10/1997 | Clement et al. | |
| 5,683,345 A | 11/1997 | Waksman et al. | |
| 5,683,359 A * | 11/1997 | Farkas et al. | 604/22 |
| 5,687,714 A | 11/1997 | Kolobow et al. | |
| 5,702,439 A | 12/1997 | Keith et al. | |
| 5,704,926 A | 1/1998 | Sutton | |
| 5,713,849 A | 2/1998 | Bosma et al. | |
| 5,843,022 A | 12/1998 | Willard et al. | |
| 5,906,590 A | 5/1999 | Hunjan et al. | |
| 5,944,686 A | 8/1999 | Patterson et al. | |
| 5,989,210 A | 11/1999 | Morris et al. | |
| 5,989,271 A * | 11/1999 | Bonnette et al. | 606/159 |
| 6,024,729 A | 2/2000 | Dehdashtian et al. | |
| 6,063,069 A | 5/2000 | Cragg et al. | |
| 6,068,623 A | 5/2000 | Zadno-Azizi et al. | |
| 6,099,496 A * | 8/2000 | Berthiaume et al. | 604/102.02 |
| 6,106,542 A | 8/2000 | DeCarlo et al. | |
| RE37,153 E * | 5/2001 | Henszey et al. | 138/26 |
| 6,224,570 B1 | 5/2001 | Le et al. | |
| 6,241,744 B1 * | 6/2001 | Imran et al. | 606/159 |
| 6,287,280 B1 | 9/2001 | Lampropoulos et al. | |
| 6,331,176 B1 | 12/2001 | Becker et al. | |
| 6,527,979 B2 | 3/2003 | Constantz et al. | |
| 6,544,220 B2 | 4/2003 | Shuman et al. | |
| 6,652,548 B2 | 11/2003 | Evans et al. | |
| 6,834,842 B2 | 12/2004 | Houde | |
| 6,875,193 B1 * | 4/2005 | Bonnette et al. | 604/22 |
| 7,226,433 B2 | 6/2007 | Bonnette et al. | |
| 2003/0069541 A1 * | 4/2003 | Gillis et al. | 604/164.01 |
| 2004/0068248 A1 | 4/2004 | Mooney et al. | |
| 2004/0210194 A1 * | 10/2004 | Bonnette et al. | 604/167.06 |
| 2006/0047239 A1 * | 3/2006 | Nita et al. | 604/22 |
| 2006/0064123 A1 | 3/2006 | Bonnette et al. | |
| 2007/0010847 A1 | 1/2007 | Pepper | |
| 2007/0073233 A1 | 3/2007 | Thor et al. | |
| 2008/0312672 A1 | 12/2008 | Bonnette et al. | |
| 2008/0319386 A1 | 12/2008 | Bonnette et al. | |

FOREIGN PATENT DOCUMENTS

| | | |
|---|---|---|
| EP | 0251512 | 1/1988 |
| EP | 0232678 | 8/1992 |
| EP | 0528181 | 2/1993 |
| GB | 1571459 | 7/1980 |
| WO | WO9005493 | 5/1990 |
| WO | WO9410917 | 5/1994 |

OTHER PUBLICATIONS

Office Action issued Oct. 14, 2009 in corresponding U.S. Appl. No. 11/891,450.

International Search Report issued Oct. 2, 2008 in corresponding International Application PCT/US08/66039.

International Search Report issued Oct. 2, 2008 in corresponding International Application PCT/US08/65736.

International Report on Patentability issued Dec. 30, 2009, in corresponding International Application PCT/US081065736.

International Report on Patentability issued Jan. 7, 2010, in corresponding International Application PCT/US081066039.

European Search Report issued Jun. 1, 1999, for corresponding application EP 99300846.

International Search Report issued Sep. 13, 2007, for corresponding application PCT/US05/41412.

* cited by examiner

FORWARDLY DIRECTED FLUID JET CROSSING CATHETER

CROSS REFERENCES TO RELATED APPLICATIONS

This application claims priority from the earlier filed U.S. Provisional Application No. 60/934,284 filed Jun. 12, 2007, entitled "Front Spray Catheter", and is hereby incorporated into this application by reference as if fully set forth herein.

BACKGROUND OF THE INVENTION

1. Field of the Invention

The present invention relates to the field of catheters, and more particularly, relates to a forwardly directed fluid jet crossing catheter used for the purpose of crossing a Chronic Total Occlusion (CTO), whereby a moderate speed and safe velocity fluid jet stream is used to wear away arterial lesions forming a CTO and advance therethrough. Chronic total occlusions are arterial lesions that have progressed to the point where there is no flow through the vessel (total occlusion). Furthermore, it is generally considered highly difficult to cross a CTO with a standard support guidewire. In other words, if a total occlusion is easily crossed with a standard guidewire, it is not a chronic total occlusion. Furthermore, coronary chronic total occlusions have been characterized as having tough fibrous and even calcific caps with a softer interior. This invention is intended to help a guidewire penetrate the chronic total occlusion by directing a moderate speed fluid jet at the occlusion.

The forwardly directed fluid jet crossing catheter is designed to cross chronic total occlusions in a peripheral or coronary artery. Bodies of scientific evidence have indicated that after opening by crossing a coronary chronic total occlusion in a patient, the patient is benefited thereby. Although the presence of a chronic total occlusion usually means there is some collateralization, opening of a chronic total occlusion provides a greater flow reserve. As a result, the opening of chronic total occlusions in a patient has been shown to have improved patient morbidity and mortality. Furthermore, a peripheral procedure can be expedited by crossing peripheral chronic total occlusions. In the case of critical limb ischemia cases, the slow progression of a peripheral artery disease may result in total occlusions in peripheral arteries that are difficult to cross with conventional wires. Other methods, such as the use of a laser, can facilitate this crossing capability for peripheral arteries depending on the amount of calcification.

2. Description of the Prior Art

The crossing of chronic total occlusions is a relatively new treatment modality. As such, the field is not mature with products that are proven in this challenging task, especially for chronic total occlusions in a coronary artery. There are a few products that are being used for this coronary treatment. In general, the first choice of physicians is the use of improved guidewires of which there are many. The Confienza Conquest wire is an example of a very stiff tip wire used to penetrate the fibrous cap of a chronic total occlusion. However, the use of this type of stiff wire for chronic total occlusions is challenging and time consuming resulting in an increased radiation exposure to the patient. Other devices that have been tried include the FrontRunner by Lumend which is a clamshell type device for mechanically opening its blunt jaws at the face of the chronic total occlusion. This device was unsuccessful some of the time so it was not seen as being reliable. Another device is the Safe Cross system from Interluminal Therapeutics. This system consists of a radio frequency ablation wire coupled with an Optical Coherence Detection device to ensure that the wire does not burn through the vessel wall. Although this system is considered generally reliable by trained professionals, it has some limitations. First, the method is slow. Second, if a channel is burned next to the vessel wall, it can be difficult to direct the wire to take an alternative path. Another device is a re-entry device by Lumend (Outback Catheter). This device provides a procedure for crossing a peripheral chronic total occlusion by purposely directing a guidewire into the subintimal space of the vessel. Once the guidewire is beyond the chronic total occlusion, the re-entry catheter directs the guidewire back into the true lumen. Although this is a novel technique, it is not uniformly accepted, nor is this type of procedure comfortable for physicians to perform. Lasers can be used to cross peripheral chronic total occlusions and can facilitate the crossing capability for peripheral arteries depending on the amount of calcification. The present invention uses a moderate speed fluid jet stream to open a passage through, i.e., to cross, a chronic total occlusion. As a result, the treatment will be cool, directable (since the device is torqueable) in the true lumen of the vessel, and rapid. Preferably, the device will find the true lumen since medium velocity fluid jet streams will naturally find a dissection plane (the easiest path) or through one or more microchannels of the chronic total occlusion. These attributes are seen as distinct advantages over competitive treatment options.

SUMMARY OF THE INVENTION

The general purpose of the present invention is to provide a forwardly directed fluid jet crossing catheter. The forwardly directed fluid jet crossing catheter uses a single saline fluid jet stream, preferably in tubular flow form and/or in solid flow form, to penetrate and advance through a chronic total occlusion. The concept for the present invention stemmed from vessel safety testing that had been done with thrombectomy catheters. Collective findings of numerous animal studies have shown that the side exhaust flow velocities from thrombectomy catheters were safe although the internal fluid jet streams were so fast that they could possibly damage an artery when it was contacted. Thrombectomy catheters, using cross stream jet technology, have two distinct sets of windows (or orifices). There is one set of inflow windows that is near the origin of the internal high velocity fluid jet streams and another set of side exhaust windows that is located proximally. The concept behind the forwardly directed fluid jet crossing catheter, which can also be referred to as a front spray catheter, is to provide a velocity that is less than the high velocity fluid jets of thrombectomy catheters that will still be safe for contacting the vessel wall, and yet higher than the side exhaust velocity of thrombectomy catheters so that it will be efficacious in penetrating through a tough organized clot.

An important feature of the present invention is the small crossing profile of the fluid jet catheter. Since the device of this invention is used to cross chronic total occlusions, the smaller the crossing profile the better the chance to successfully navigate across the lesion. Therefore, an exhaust lumen as used in cross stream technology becomes a feature that is not used in order to reduce and minimize the crossing profile.

The invention uses a proximal catheter and a connected smaller diameter distal catheter which, for the most part, form a low pressure cavity and a high pressure cavity, respectively, through which a guidewire tube and a high pressure tube generally align. The distal end of the high pressure tube terminates in the high pressure cavity to communicate with and to pressurize the high pressure cavity. An entry hole is included in the distal region of the guidewire tube where such entry hole is located in the high pressure cavity to provide communication between the high pressure cavity and the lumen of the guidewire tube. High pressure fluid emanating from the lumen of the high pressure tube pressurizes the high pressure cavity, whereby the high pressure fluid passes through the entry hole in the guidewire tube and passes into the lumen of the guidewire tube to surround a co-located guidewire. Thence, the high pressure fluid flows distally along the remaining lumen space, as well as along the guidewire, in a cylindrical flow form to emanate from the guidewire lumen as a distally directed fluid jet stream having cylindrical flow form. The guidewire can be retracted a short distance to influence the shape of the cylindrical flow. The forwardly directed fluid jet crossing catheter is essentially a guide catheter with a reduced radius distal end in the form of a distal catheter tube. The distal catheter tube has co-located components which comprise a formable and shapeable catheter tip region. The device can be deployed over a standard guidewire if the physician finds difficulty crossing a lesion. The small diameter of the distal end ensures that a strong cylindrical flow fluid jet stream forms around the guidewire. By torqueing the forwardly directed fluid jet crossing catheter, the optionally bent tip can be directed along and navigate a tortuous anatomy. The velocity of the emanated fluid jet stream can be modified not only by adjusting the pumping speed of a drive unit, but also the velocity and flow rate of the fluid jet stream can be influenced by the amount of engagement of the guidewire within the guidewire tube which is located, in part, within the reduced radius distal catheter tube. For example, if the guidewire is repositioned proximally into the catheter, more of the distal lumen becomes available since there is no guidewire contained therein whereby the jet volume is increased.

According to one or more illustrations of the present invention, there is provided a forwardly directed fluid jet crossing catheter having features and components including a manifold and closely associated components located therein and thereupon, a proximal catheter tube, a smaller distal catheter tube attached to and extending from the proximal catheter tube, an internal adhesive plug seal in the proximal portion of the distal catheter tube separating the lumens of the proximal catheter tube and the distal catheter tube, a low pressure cavity extending proximally from the adhesive plug seal and along the lumen of the proximal catheter tube connecting and communicating with a manifold in a low pressure region, a high pressure cavity extending distally from the adhesive plug seal and along the lumen of the distal catheter tube to and including a tapered tip and tapered tip lumen, a high pressure tube attached to and extending generally from the manifold through the lumen of the proximal catheter tube and co-located low pressure cavity, through the adhesive plug seal and into the lumen of the distal catheter tube and co-located high pressure cavity to openly terminate in the distal region of the high pressure cavity, a guidewire tube attached to and extending generally from the manifold through the lumen of the proximal catheter tube and co-located low pressure cavity, through the adhesive plug seal and into the lumen of the distal catheter tube and co-located high pressure cavity to openly terminate at the distal end of the high pressure cavity, and an entry hole in the distal region of the guidewire tube which is located in the high pressure cavity to provide communication between the high pressure cavity and the lumen of the guidewire tube.

One significant aspect and feature of the forwardly directable fluid jet crossing catheter is a minimal reduced distal cross section in order to enhance the ability to cross chronic total occlusions in small or narrow vascular regions.

Another significant aspect and feature of the present invention is the use of a forwardly directed fluid jet stream in combination with a formable and shapeable catheter tip region.

Still another significant aspect and feature of the present invention is a formable and shapeable catheter tip region having a section of annealed high pressure tube within a distal catheter tube and a flexible tapered tip providing a directable and shapeable atraumatic tip where such formable and shapeable catheter tip region can positively influence tracking along the vasculature.

Still another significant aspect and feature of the present invention is a forwardly directed fluid jet crossing catheter with a flexible tapered tip that gradually transitions substantially to the diameter of a guidewire to aid in tracking and in crossing a chronic total occlusion.

Yet another significant aspect and feature of the present invention is the positioning of a guidewire within a guidewire lumen to influence the velocity and/or flow rate and the structure of a fluid jet stream.

Still another significant aspect and feature of the present invention is a forwardly directed jet stream delivered in a cylindrical flow fashion about a guidewire.

Still another significant aspect and feature of the present invention is a forwardly directed fluid jet crossing catheter having a dedicated guidewire lumen along the entire length of the catheter so that guidewires can be exchanged.

Yet another significant aspect and feature of the present invention is the use of a proximal catheter tube generally forming a low pressure cavity.

Yet another significant aspect and feature of the present invention is the use of a distal catheter tube generally forming a high pressure cavity.

Yet another significant aspect and feature of the present invention is the use of an adhesive plug injected through a hole in the distal catheter tube to substantially and separatingly seal the lumens of the distal catheter tube and the proximal catheter tube in order to substantially provide a high pressure cavity and a low pressure cavity.

Yet another significant aspect and feature of the present invention is a forwardly directed fluid jet crossing catheter that isolates a high pressure cavity from the manifold of the catheter by the use of an interceding low pressure cavity.

Still another significant aspect and feature of the present invention is the use of a high pressure tube connected to and extending from a manifold and through the co-located proximal catheter tube and low pressure cavity, through an adhesive plug seal and thence into and openly terminating in the high pressure cavity.

Still another significant aspect and feature of the present invention is the use of a guidewire tube connected to and extending from a manifold and through the co-located proximal catheter tube and low pressure cavity, through an adhesive plug seal and thence into and terminating beyond the high pressure cavity.

Still another significant aspect and feature of the present invention is the use of an entry hole in the distal region of the guidewire tube which communicates with the high pressure cavity of the distal catheter tube to provide for entry of high pressure fluid into the guidewire tube.

Still another significant aspect and feature of the present invention is the use of a high pressure cavity for transfer of high pressure fluid from the lumen of a high pressure tube through the entry hole of the guidewire tube to provide a cylindrical flow of a high pressure fluid distally along the portion of the guidewire lumen not occupied by a co-located guidewire, as well as a cylindrical flow along the co-located guidewire.

Yet another significant aspect and feature of the present invention is an internal high pressure tube sealed inside one or more guide catheter tubes for the purpose of delivering pressurized saline to a formable and shapeable catheter tip region.

Yet another significant aspect and feature of the present invention is the use of a portion of a guidewire tube to deliver high pressure fluid to a chronic total occlusion.

Having thus briefly described embodiments of the present invention and having mentioned some significant aspects and features of the present invention, it is the principal object of the present invention to provide a forwardly directed fluid jet crossing catheter.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
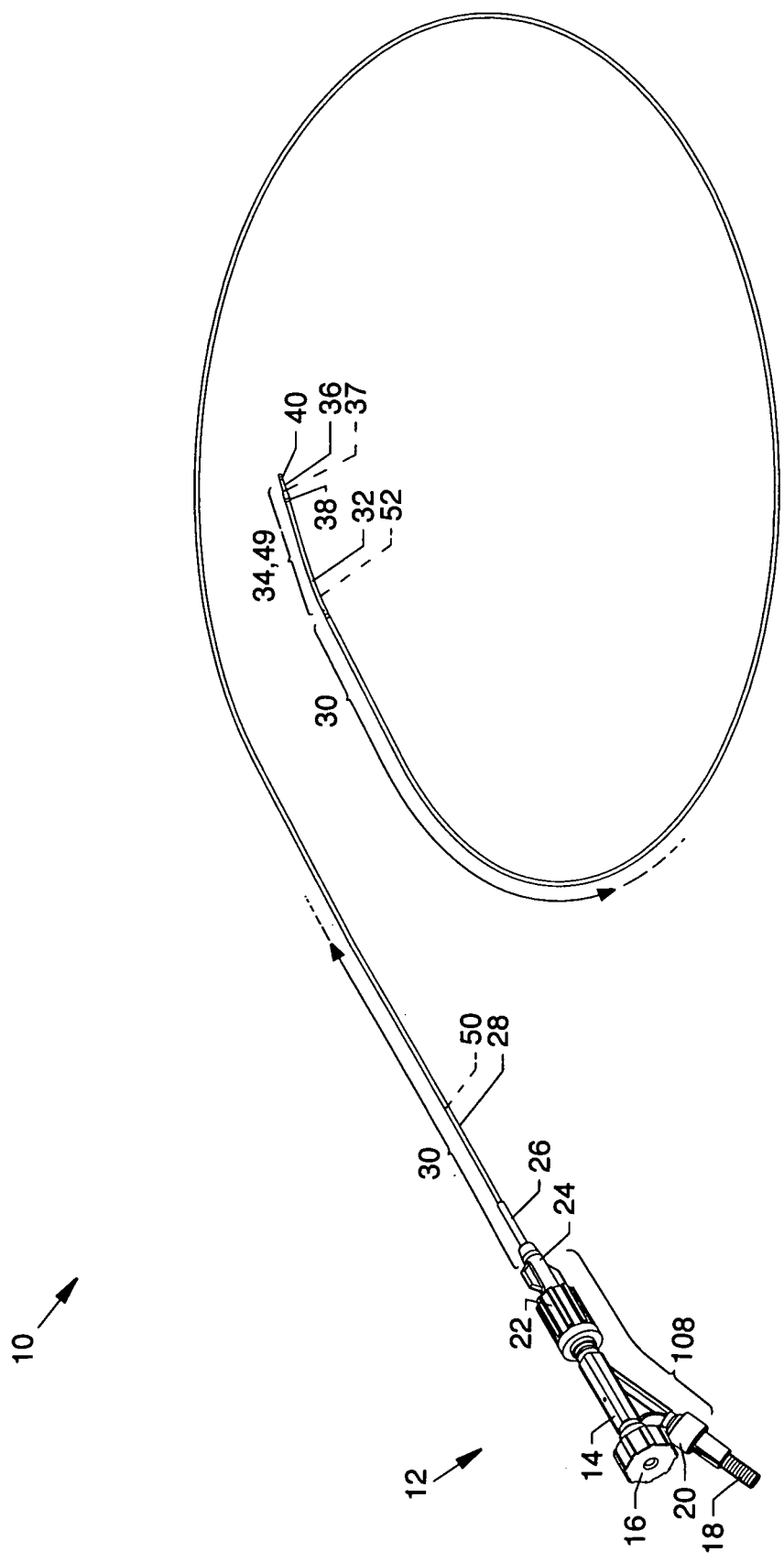
FIG. 1 is an isometric view of a forwardly directed fluid jet crossing catheter, the present invention.
Figure 2:
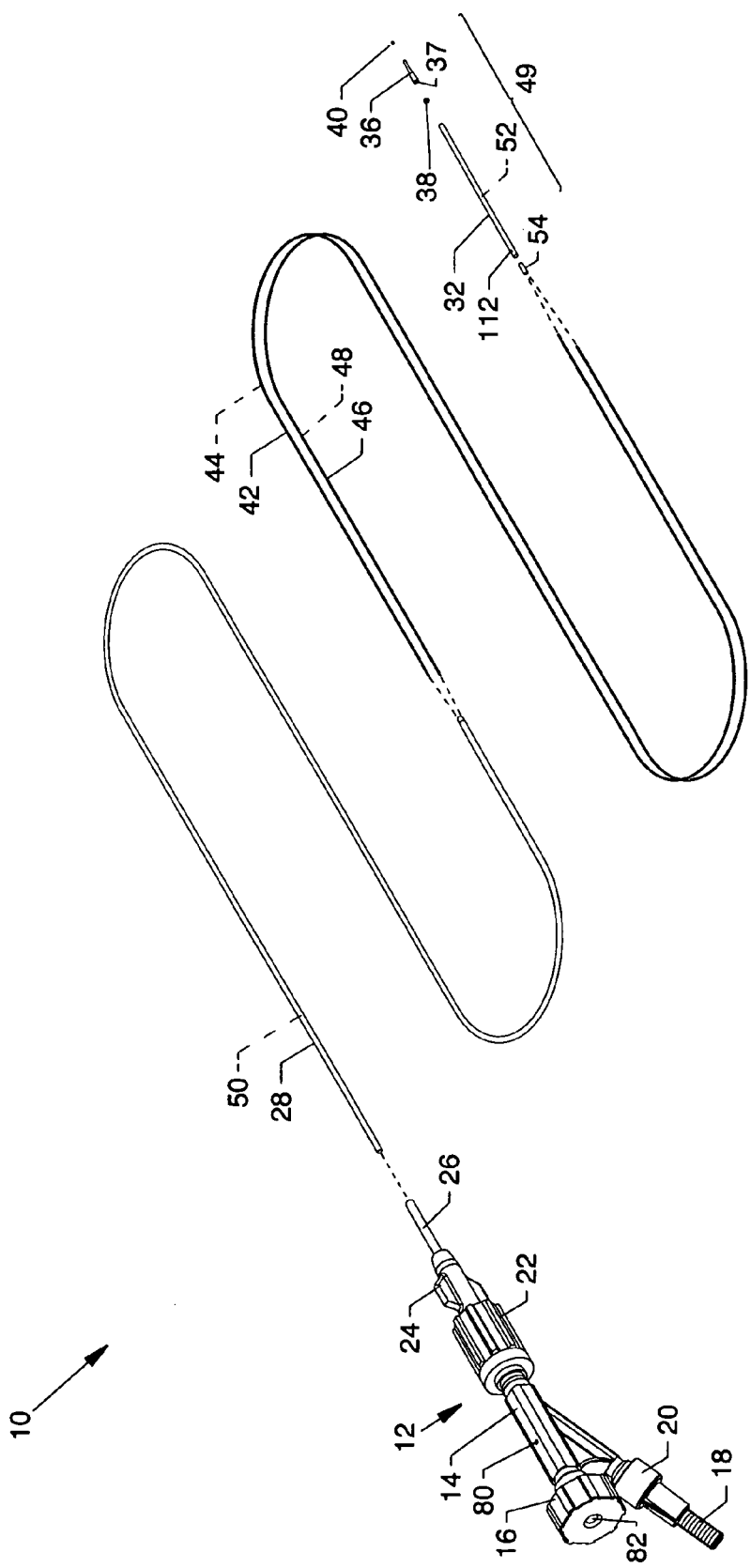
FIG. 2 is an isometric view of the present invention where the components distal to a manifold are shown in exploded view.

FIG. 1 is an isometric view of a forwardly directed fluid jet crossing catheter 10, the present invention, and FIG. 2 is an isometric view of the invention where the components distal to a manifold 12 are shown in exploded view. Readily identifiable components at the proximal region of the invention include, but are not limited to, the manifold 12 having closely associated components including a central body 14, a hemostasis valve 16, a high pressure connector 18, a Luer fitting 20, a Luer connector 22, a winged Luer fitting 24, and a strain relief tube 26. Other components of the invention extend from the interior of the manifold 12 and through the strain relief tube 26 in succession in a distal direction including, but not limited to, a torqueable and flexible (4 French) proximal catheter tube 28, preferably of Pebax®, which, in general, delineates the greater portion of a low pressure cavity 30 (FIG. 1), another torqueable and short reduced diameter flexible and shapeable low profile (3 French) distal catheter tube 32, preferably of Pebax®, which, in general, delineates the greater portion of a high pressure cavity 34 (FIG. 1) extending along the distal catheter tube 32 and along a flexible tapered tip 36 having a lumen 37 attached to the distal end of the distal catheter tube 32. Marker bands 38 and 40 are located over and about the opposing ends of the tapered tip 36. The marker band 38 is securingly aligned over the overlapping coaxial junction of the proximal end of the tapered tip 36 and the distal end of the distal catheter tube 32, and the marker band 40 is securingly aligned over the overlapping coaxial junction of the distal end of the tapered tip 36 and the distal end of the guidewire tube 42.

The proximal ends of a guidewire tube 42 having a lumen 44 (FIG. 2) and a high pressure tube 46 having a lumen 48 (FIG. 2) are aligned and secured within the manifold 12, as later described in detail. The central and greater portions of the guidewire tube 42 and the high pressure tube 46 are aligned in a lumen 50 of the proximal catheter tube 28 and also extend to align in the proximal portion of the lumen 52 of the distal catheter tube 32 where such a proximal portion of the lumen 52 is proximal to an adhesive plug seal 54 (FIG. 6), i.e., the central and greater portions of the guidewire tube 42 and the high pressure tube 46 are aligned within the low pressure cavity 30. The distally located shorter portions of the guidewire tube 42 and the high pressure tube 46 are aligned and extend within the distal portion of the lumen 52 of the distal catheter tube 32, where such a distal portion of the lumen 52 is distal to the adhesive plug seal 54, and are secured therein by the use of the adhesive plug seal 54 in the distal catheter tube 32. In addition, the distal end of the guidewire tube 42 extends further into and is secured in the lumen 37 of the tapered tip 36 by the marker band 40, as shown in FIG. 6, i.e., the distally located shorter portions of the guidewire tube 42 and the high pressure tube 46 are fully or partially aligned within the high pressure cavity 34 formed by the distal catheter tube 32 and the lumen 37 of the flexible tip 36. The low pressure cavity 30 is associated generally with the proximal catheter tube 28 and the high pressure cavity 34 is generally associated with the lumen 52 of the distal catheter tube 32 and with the lumen 37 of the flexible tapered tip 36, as shown in detail in FIGS. 5 and 6.

Figure 3:
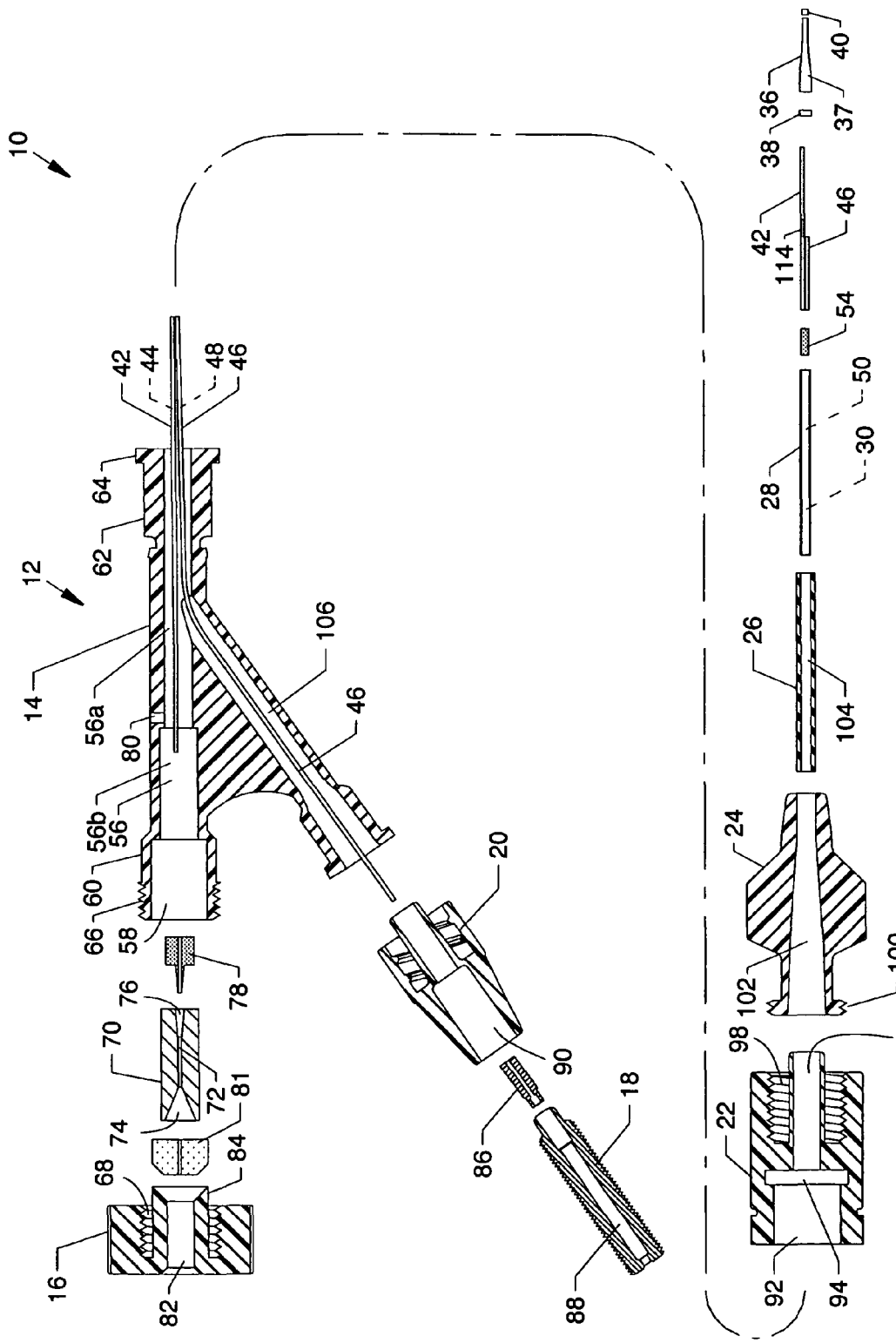
FIG. 3 is an exploded view of the manifold and closely associated components.
Figure 4:
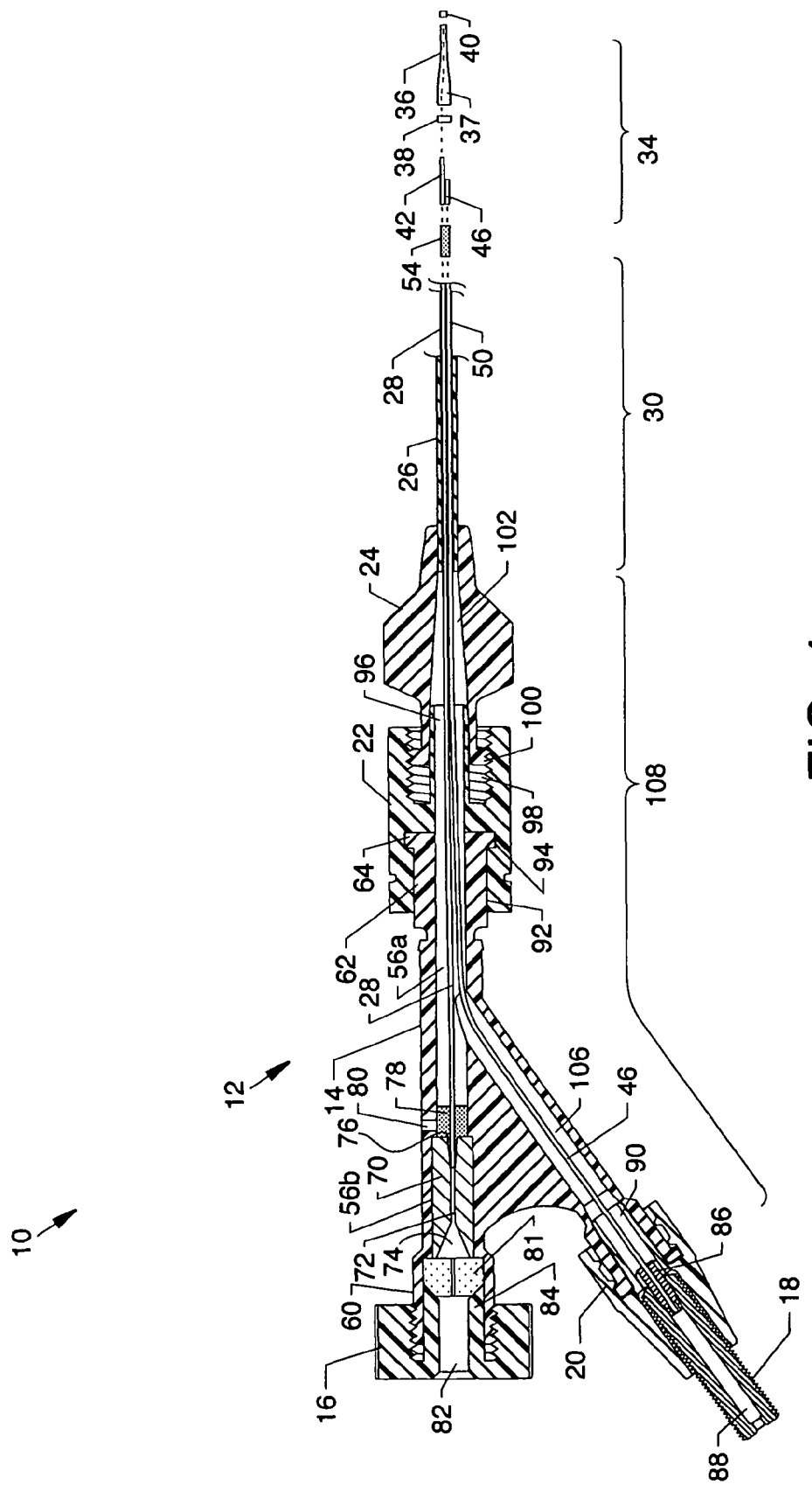
FIG. 4 is a view of the assembled components of FIG. 3.

FIG. 3 is an exploded view of the manifold 12 and its closely associated components, and FIG. 4 is a view of the assembled components of FIG. 3. With reference to FIGS. 3 and 4, the instant invention is further described. The manifold 12 includes connected and communicating passageways and cavities located along and about the central body 14 including a central passageway 56 having a small radius passageway section 56a and a connected large radius passageway section 56b, the latter connecting to a proximally located cylindrical cavity 58 located in a cavity body 60. The small radius passageway section 56a extends through a distal tubular body 62 and an annular connector flange 64. Threads 66 are located about the proximal exterior portion of the cavity body 60 at the proximal region of the manifold 12 for accommodation of internal threads 68 of the hemostasis nut 16. A guidewire tubular adapter 70 has multiple connected features including a central bore 72, a proximally located conical guide passageway 74 communicating with the central bore 72, and a distally located tapered bore 76 communicating with the central bore 72. The guidewire tubular adapter 70 is aligned in and housed in the large radius passageway section 56b in the proximal region of the manifold 12. The proximal end of the guidewire tube 42 extends into the tapered bore 76 for anchoring and also into the central bore 72 of the guidewire tubular adapter 70. An adhesive 78 is injected through an injection hole 80 to flow into the tapered bore 76 and to surround and positionally fix the proximal region of the guidewire tube 42 within the tapered bore 76 of the guidewire tubular adapter 70. The injected adhesive 78 also flows into and about the proximal end of the small radius passageway section 56a and around and about the guidewire tube 42. Such positional fixing of the guidewire tube 42 within the tapered bore 76 and in the small radius passageway section 56a ensures the alignment of the most proximal section of the guidewire tube 42 within the central bore 72. The guidewire tubular adapter 70 is used to guide the distal end of a guidewire 120 (FIG. 9) for passage into the lumen 44 of the guidewire tube 42, and thence indirectly through the manifold 12 and other distally located components to exit from the tapered tip 36. A seal 81 for sealing about and against a guidewire is located in the distal portion of the cavity 58 in intimate contact with the proximal end of the guidewire tubular adapter 70. The hemostasis nut 16 includes a centrally located passageway 82 extending through a centrally located cylindrical boss 84, the latter of which exerts pressure against the seal 81 when the threads 68 of the hemostasis nut 16 are engaged with and advanced along the threads 66 of the cavity body 60. A seal is also effected in the absence of a guidewire. Although one method of sealing against a guidewire is briefly shown and described, it is appreciated that other methods can be incorporated into this and other forms of the instant invention, such as disclosed in the referenced U.S. Pat. No. 7,226,433 entitled "Thrombectomy Catheter Device Having a Self-Sealing Hemostasis Valve."

A ferrule 86 is aligned and secured within a passageway 88 of the threaded high pressure connector 18, the combination of which is partially aligned within a passageway 90 of the Luer fitting 20. The proximal end of the proximal high pressure tube 46, which is utilized for delivery of high pressure ablation liquids, is suitably secured in an internal passageway of the ferrule 86 to communicate with the interior passageway 88 of the threaded high pressure connector 18, as shown in FIG. 4. A plurality of components distal to the manifold 12 is secured directly or indirectly to the annular connector flange 64 of the manifold 12 and includes, but is not limited to, the Luer connector 22, the Luer fitting 24, and the strain relief tube 26. The Luer connector 22 includes an annular proximal cavity 92, an annular connector recess 94, a proximal tubular passageway 96, and internal threads 98 offset from the tubular passageway 96. The Luer fitting 24 includes proximally located threads 100 for engagement with the internal threads 98 of the Luer connector 22 and also includes a centrally located partially tapered passageway 102. The strain relief tube 26 includes an internal passageway 104. The proximal end of the proximal catheter tube 28 is coaxially aligned with and is suitably secured directly within the internal passageway 104 of the strain relief tube 26 and indirectly within the distal untapered portion of the partially tapered passageway 102 of the Luer fitting 24, whereby the lumen 50, i.e., the low pressure cavity 30 of the proximal catheter tube 28, communicates with the partially tapered passageway 102 of the Luer fitting 24, the tubular passageway 96 of the Luer connector 22, the small radius passageway section 56a, the adhesive 78, a high pressure connection branch passageway 106, and the passageway 90 of the Luer fitting 20. Together, the combined structure of the partially tapered passageway 102 of the Luer fitting 24, the tubular passageway 96 of the Luer connector 22, the small radius passageway section 56a, the adhesive 78, the high pressure connection branch passageway 106, and the passageway 90 of the Luer fitting 20 form a manifold low pressure region 108 (FIG. 4). The manifold low pressure region 108 is connected to and in direct communication with the low pressure cavity 30 of the proximal catheter tube 28. The low pressure cavity 30 includes the section of the lumen 50 of the proximal catheter tube 28 extending distally from the proximal end of the proximal catheter tube 28 to the point of an intersection with the proximal end of the distal catheter tube 32 and the associated section of the lumen 52 of the distal catheter tube 32 and also includes the section from the point of intersection of the proximal catheter tube 28 and the distal catheter tube 32 and associated lumen portions extending to the proximal end of the adhesive plug seal 54. The high pressure tube 46 also extends from the ferrule 86, through the high pressure connection branch passageway 106, through part of the small radius passageway section 56a, through the distal tubular body 62, through the Luer connector 22, through the Luer fitting 24, and indirectly through the lumen 104 of the strain relief tube 26. Thence, the high pressure tube 46 extends through the lumen 50 of the proximal catheter tube 28 and the proximal end of the lumen 52 of the distal catheter tube 32, i.e., the low pressure cavity 30, and then extends through the adhesive plug seal 54. The high pressure tube 46 continues further into the high pressure cavity 34, i.e., the portion of the distal catheter tube 32 lumen 52 distal to the adhesive plug seal 54 to terminate proximal to the tapered tip 36, as shown in detail in FIGS. 5 and 6. The guidewire tube 42 extends generally parallel to the high pressure tube 46. The proximal end of the guidewire tube 42 extends into the tapered bore 76 of the guidewire tubular adapter 70 for anchoring and into the central bore 72 of the guidewire tubular adapter 70 and fixed in position by the adhesive 78, as previously described, and also through part of the small radius passageway section 56a and anchored therein by the use of the adhesive 78, through the distal tubular body 62, as previously described, through the Luer connector 22, through the Luer fitting 24, and through the lumen 104 of the strain relief tube 26. Thence, the guidewire tube 42 extends through the lumen 50 of the proximal catheter tube 28 and into the proximal end of the lumen 52 of the distal catheter tube 32, i.e., the low pressure cavity 30. The guidewire tube 42 then extends through the adhesive plug seal 54 and continues into the portion of the lumen 52 of the distal catheter tube 32, distal to the adhesive plug seal 54, and further within the lumen 37 of the tapered tip 36 to finally terminate and be secured within the distal end of the tapered tip 36, i.e., the guidewire tube 42 extends into and resides in the high pressure cavity 34, as shown in detail in FIGS. 5 and 6.

Figure 5:
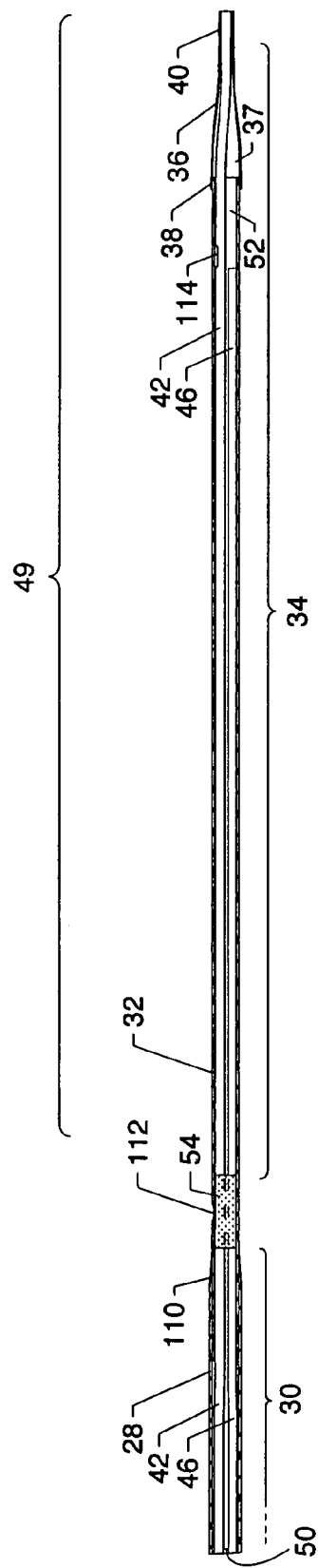
FIG. 5 is a partial cross section view showing the relationship of a distal catheter tube to a proximal catheter tube of the present invention.
Figure 6:
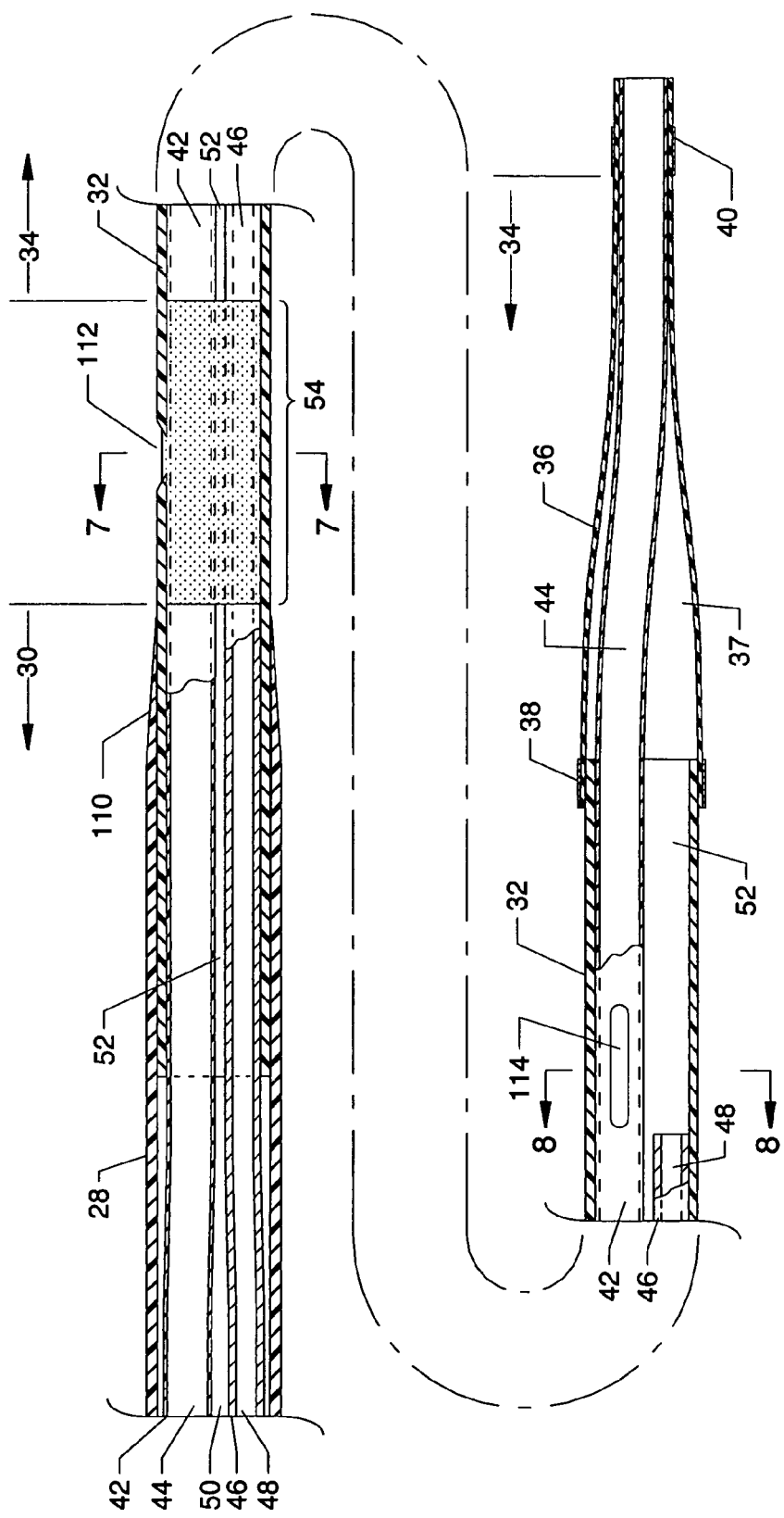
FIG. 6 is a detailed partial cross section view of the components of FIG. 5.

FIG. 5 is a partial cross section view showing the relationship of the distal catheter tube 32 to the proximal catheter tube 28, as well as other important features of the invention. FIG. 6 is a detailed partial cross section view of the components of FIG. 5. Especially shown are the structures forming the distal end of the low pressure cavity 30 and the structure forming the high pressure cavity 34. The distal end of the proximal catheter tube 28, which includes a tapered transition 110, is coaxially aligned and suitably secured to the proximal end of the distal catheter tube 32 in an overlapping relationship.

The guidewire tube 42 and the high pressure tube 46 are shown extending along several areas or locations:

(1) portions of the guidewire tube 42 and the high pressure tube 46 are both shown at the distal end of the low pressure cavity 30 and are both aligned (a) within the distal portion of lumen 50 of the proximal catheter tube 28, and (b) are both aligned in the proximal portion of lumen 52 of the distal catheter tube 32, proximal to the adhesive plug seal 54;

(2) a portion of the guidewire tube 42 and the high pressure tube 46 are both shown encapsulated and affixed directly within the distal catheter tube 32 by the adhesive plug seal 54 which is preferably injected, in a fluid state, through an injection hole 112 in the distal catheter tube 32 and which is subsequently hardened or cured;

(3) the high pressure tube 46 is shown in the high pressure cavity 34 (a) aligned distal to the adhesive plug seal 54 and extending distally along a greater portion of the lumen 52 of the distal catheter tube 32, and (b) openly terminating a short distance proximal to the tapered tip 36; and, (4) a portion of the guidewire tube 42 is shown in the high pressure cavity 34 (a) aligned distal to the adhesive plug seal 54 and extending distally along the lumen 52 of the distal catheter tube 32, and (b) extending beyond the end of the high pressure tube 46 into and securing within the lumen 37 of the tapered tip 36 by the compression of the marker band 40 about the distal end of the tapered tip 36.

An entry hole 114, which is preferably elongated, extends through the wall of the guidewire tube 42 to provide communication between the lumen 44 of the guidewire tube 42 and the region outside of the guidewire tube 42, and more specifically, to provide communication between the lumen 44 of the guidewire tube 42 with the high pressure cavity 34 with which the lumen 48 of the high pressure tube 46 also communicates. Communication also occurs between the lumen 48 of the high pressure tube 46 and the lumen 44 of the guidewire tube 42 through the common high pressure cavity 34, whereby a high pressure fluid is distally emanated as a high pressure fluid jet through the extreme distal end of the guidewire tube 42. Consideration is also given to the torqueability and flexibility of the proximal catheter tube 28 and the distal catheter tube 32 by the use of braided Pebax® tubing for each. Consideration is given to flexibility by the use of a polyimide for construction of the guidewire tube 42. Consideration is also given for shapeability and directability as provided by a formable and shapeable catheter tip region 49 (FIG. 5). Such a provision is made along the distal catheter tube 32 by the use of a flexible tapered tip 36 and by the use of a flexible high pressure tube 46, preferably of stainless steel, which is annealed along a distal portion thereof in order that a curved shape may, if desired, be manually imparted by a physician to the high pressure tube 46 and the surrounding distal catheter tube 32 for negotiating within tortuous vascular passages.

Figure 7:
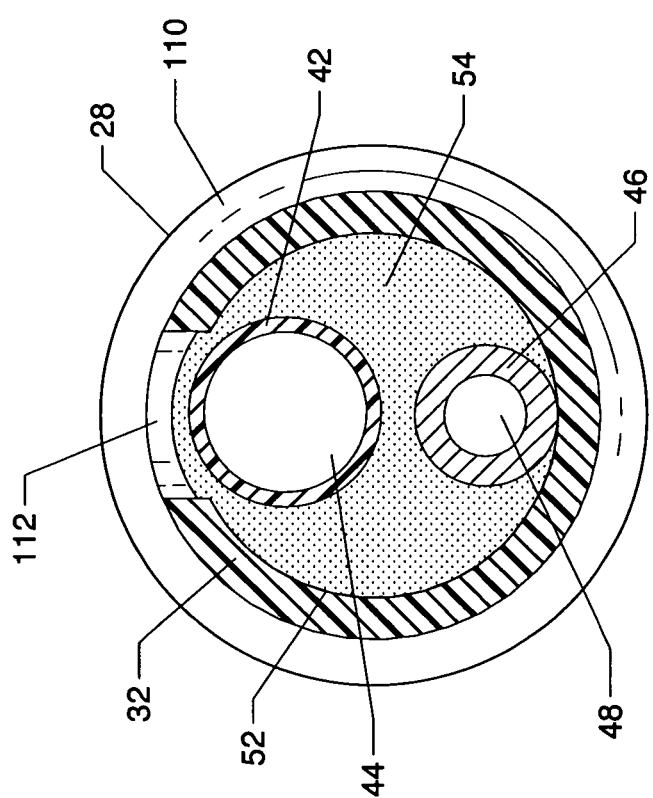
FIG. 7 is a cross section view along line 7-7 of FIG. 6 showing the fixation, surrounding and encapsulation of a guidewire tube and a high pressure tube within a distal catheter tube by an adhesive plug seal.

FIG. 7 is a cross section view along line 7-7 of FIG. 6 showing the fixation surrounding and encapsulation of the guidewire tube 42 and the high pressure tube 46 within the distal catheter tube 32 by the adhesive plug seal 54.

Figure 8:
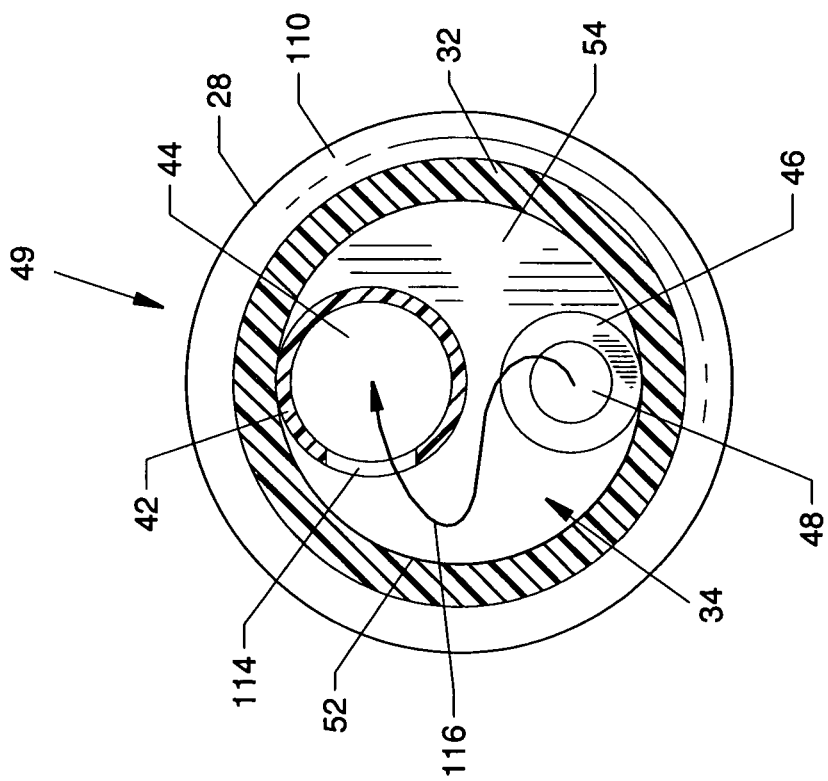
FIG. 8 is a cross section view along line 8-8 of FIG. 6 showing the relationship of a guidewire tube and a high pressure tube within a distal catheter tube and to the high pressure cavity.

FIG. 8 is a cross section view along line 8-8 of FIG. 6 showing the relationship of the guidewire tube 42 and the high pressure tube 46 within the distal catheter tube 32 and to the high pressure cavity 34. The flow of high pressure fluid 116 is within the high pressure cavity 34 and is demonstrated emanating from the lumen 48 of the high pressure tube 46 through the high pressure cavity 34, through the entry hole 114 and then into the lumen 44 of the guidewire tube 42 for distally directed emanation therefrom as a cylindrical fluid jet stream 122, as shown in FIG. 9.

Mode of Operation

Figure 9:
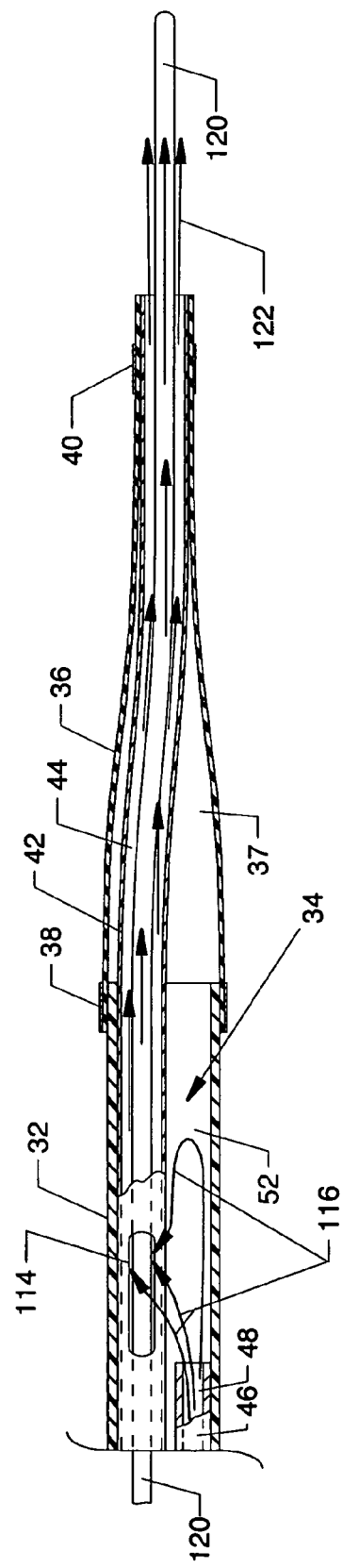
FIG. 9 is a cross section view of the distal end of the distal catheter tube showing the flow of high pressure fluid from the lumen of the high pressure tube into the high pressure cavity, whereby the entire high pressure cavity is pressurized.

FIG. 9 is a cross section view of the distal end of the distal catheter tube 32 and the tapered tip 36 showing the flow of the high pressure fluid 116, preferably in the form of a saline or other suitable solution, from the lumen 48 of the high pressure tube 46 into the high pressure cavity 34, whereby the entire high pressure cavity 34 is pressurized. A guidewire 120 is shown residing in the lumen 44 of the guidewire tube 42 and extending directly through the distal end of the lumen 44, as well as extending indirectly through and beyond the tapered tip 36. The high pressure fluid 116 in the pressurized high pressure cavity 34 forcibly enters the entry hole 114 in the guidewire tube 42 and surrounds the guidewire 120 and is contained within the portion of the lumen 44 unoccupied by the guidewire 120 to flow along the path of least resistance along and between the unoccupied tubular space in the lumen 44 provided between the guidewire 120 and the guidewire tube 42. The high pressure fluid 116 emanates as a high velocity, cylindrical flow, jet stream 122 from the distal end of the lumen 44 in a distal direction preferably along and coaxial to the guidewire 120 in the form of a cylindrical flow. Preferably, the distal end of the high pressure tube 46 is in close proximity to the entry hole 114 in the guidewire tube 42 in order to provide for the shortest path therebetween and thus obtain maximum efficacy and efficiency. The adhesive plug seal 54 (FIG. 5) prevents the high pressure fluid 116 from entering the low pressure cavity 30. Sealing of the manifold 12 about a guidewire can be accomplished by the use of simplified or generic components, such as, but not limited to, the hemostasis valve 16 and the seal 81, as required. Proximal flow of pressurized saline through the lumen 44 of the guidewire tube 42 is minimized due to the length of the guidewire tube 42 and the resistance to saline flow offered by the occupying guidewire 120. Any proximal saline flow is resisted by the use of the seal 81 located in the manifold 12.

Figure 10:
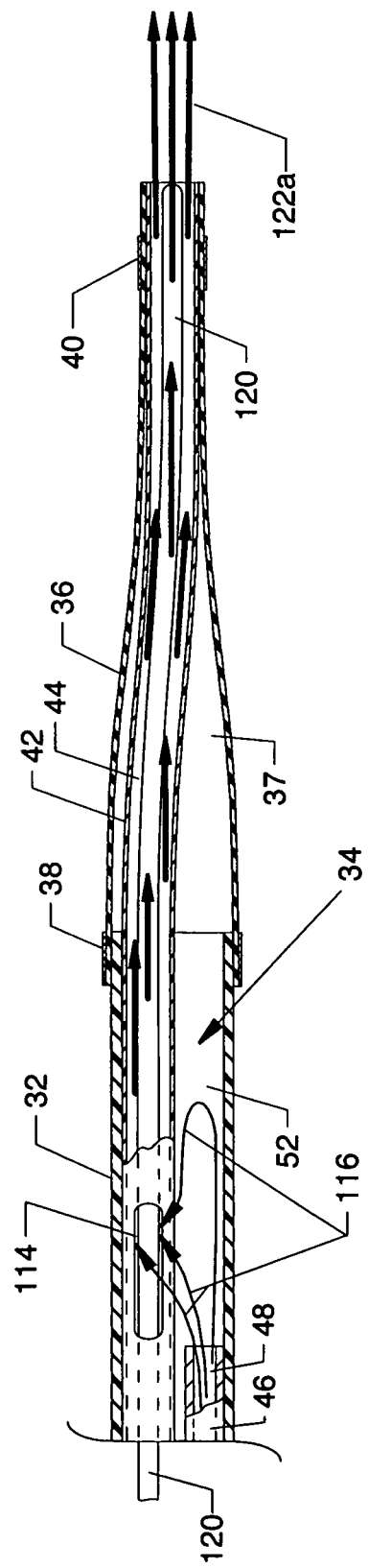
FIG. 10 is a view like FIG. 9 showing a distal tip of the guidewire repositioned proximally to a position at the distal end of the guidewire tube.

FIG. 10 is a view like FIG. 9 showing the distal tip of the guidewire 120 repositioned in close proximity to the distal end of the guidewire tube 42. Such a configuration provides for the maximum flow of a high pressure fluid 116 through the lumen 44 as a cylindrical flow jet stream 122a emanating from the lumen 44.

Figure 11:
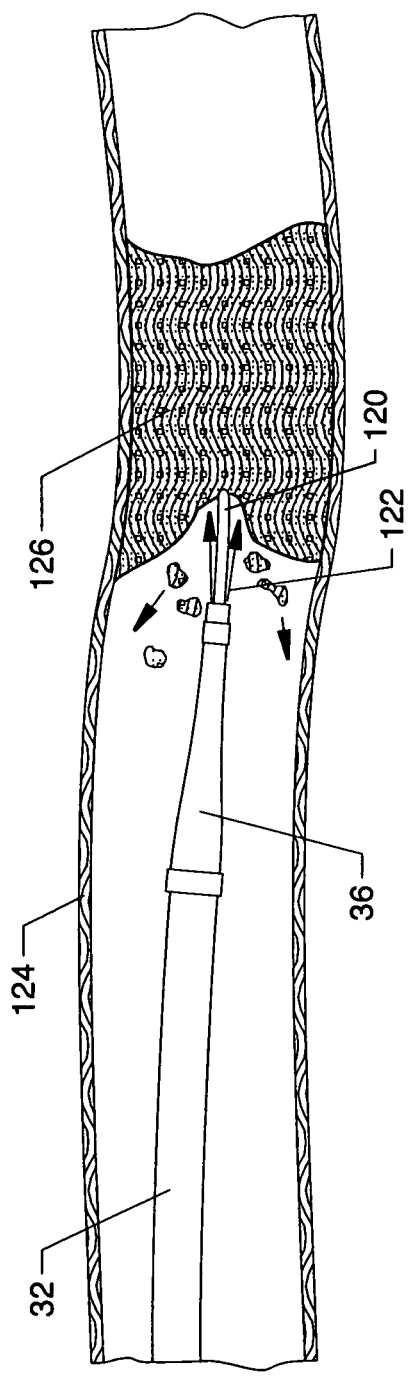
FIG. 11 shows the distal end of the distal catheter tube and the flexible tapered tip of the forwardly directed fluid jet crossing catheter aligned in a patient's vessel having a chronic total occlusion; and, FIG. 12 illustrates a crossing in the form of a channel, path or the like formed by the use of the present invention where such a crossing is formed between and extends from a proximal location of the chronic total occlusion to a distal location of the chronic total occlusion.

FIG. 11 shows the distal end of the distal catheter tube 32 and the flexible tapered tip 36 of the forwardly directed fluid jet crossing catheter 10 aligned within a patient's vessel 124 having a chronic total occlusion 126. The distal end of a guidewire 120 is positioned in close proximity to or in intimate contact with the proximal region of the chronic total occlusion 126. The guidewire 120 is aligned along the interior length of the forwardly directed fluid jet crossing catheter 10; more precisely, the guidewire 120 is aligned within the manifold 12 and closely associated components thereof, indirectly within the proximal catheter tube 28 and the distal catheter tube 32, indirectly within the low pressure cavity 30 and high pressure cavity 34, indirectly within the lumen 37 of the tapered tip 36, and directly within the lumen 44 of the guidewire tube 42, as previously described. For purposes of example and illustration, the tapered tip 36 is shown positioned at or near the chronic total occlusion 126 where a fluid jet stream, preferably the cylindrical fluid jet stream 122, is directed distally along the guidewire 120 toward the chronic total occlusion 126 in order to impinge the chronic total occlusion 126 to form and provide a path through the chronic total occlusion 126, thereby forming a crossing therethrough. The fluid jet stream 122 provides a moderate velocity cylindrical flow along the outer surface of the guidewire 120, as also shown in FIG. 9, or can provide an increased volume cylindrical flow fluid jet stream 122a when the distal end of the guidewire 120 is repositioned, as described with reference to FIG. 10. Moving the guidewire 120 between the positions shown and described in FIGS. 9 and 10 can produce various velocities and various volume fluid jet streams having different flow shapes and properties. The medium velocity fluid jet stream 122 having a cylindrical flow is produced as shown in FIG. 9 which jet stream flows within the lumen 44 and about the guidewire 120 to provide a cylindrical flow coaxially along a portion of the guidewire 120 external to the lumen 44 of the guidewire tube 42. Positioning of the proximal end of the guidewire 120, such as shown in FIG. 10, will produce a maximum velocity of the cylindrical flow fluid jet stream 122a which does not flow externally along the guidewire 120 having a greater velocity than the fluid jet stream 122 shown in FIG. 9.

Figure 12:
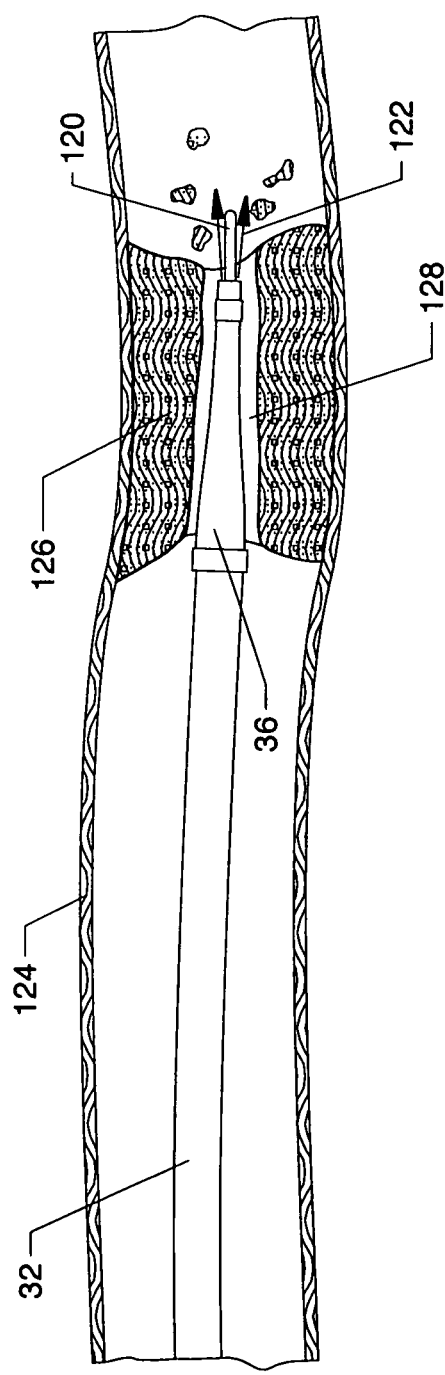

FIG. 12 illustrates a crossing 128 of the chronic total occlusion 126 in the form of a channel, path or the like resulting in the use of this invention where such a crossing 128 is formed through and extends from a proximal location of the chronic total occlusion 126 to a distal location of the chronic total occlusion 126. The moderate velocity fluid jet stream jet 122, having a cylindrical flow, is emitted from the tapered tip 36, i.e., from the lumen 44 of the guidewire tube 42, will find a dissection plane or microchannel path in the fibrous material of the chronic total occlusion 126 as directed along and about the guidewire 120. The distal end of the forwardly directed fluid jet crossing catheter 10 can be alternatingly advanced or retracted longitudinally within the chronic total occlusion 126 as the softer tissue of the chronic total occlusion 126 is eroded and dislodged from the main body of the chronic total occlusion 126 to progressively advance through the chronic total occlusion 126. During such progressive advancement, the position of the guidewire 120 can be modulated to produce various velocities and volumes in order to erode and carry loosened matter from the site of the chronic total occlusion 126, as shown in FIG. 12. The compatibility of the forwardly directed fluid jet crossing catheter 10 with 0.014 inch guidewires means that a physician could use the forwardly directed fluid jet crossing catheter 10 in combination with other chronic total occlusion devices. A very stiff tip guidewire could be used to help breach the fibrous cap (chronic total occlusion 120) and the forwardly directed fluid jet crossing catheter 10 could be used to help support the guidewire and to generate a channel or crossing once the fibrous cap had been breached. A different combination would be the use of a forwardly directed fluid jet crossing catheter 10 with other systems, such as with the use of an RF guidewire, to help breach the chronic total occlusion 126 and an RF visualization system could be used to visualize and safely check the path while the forwardly directed fluid jet crossing catheter 10 to expeditiously open a crossing 128 at the chronic total occlusion 126.

This invention describes a catheter used for purposes of crossing chronic total occlusions. The forwardly directed fluid jet crossing catheter 10 is compatible with and can be driven by the AngioJet® console (often referred to as the AngioJet® Ultra System) described in patent application Ser. No. 11/237,558 filed Sep. 28, 2005, entitled "Thrombectomy Catheter Deployment System", which is pending. The forwardly directed fluid jet crossing catheter 10 can also be incorporated into use with various support components known in the art. AngioJet® thrombectomy catheters use high velocity jets to generate strong secondary flows to liberate, macerate and remove thrombus. The system includes a roller pump to ensure that the waste flow is equivalent to the volumetric flow rate of saline pumped into the patient via the high velocity jets known as isovolumetric flow. In the case of the forwardly directed fluid jet crossing catheter 10, a single mid-range velocity fluid stream jet can be directed forward to seek a path through the chronic total occlusion 126. The forwardly directed fluid jet crossing catheter 10 may not necessarily have a waste flow that comes out of the patient, so it is not necessarily an isovolumetric catheter.

The typical mode of operation for crossing a coronary CTO is a planned procedure which is typically not an emergency situation. In general, a patient with a known chronic total occlusion means that there was a previously failed attempt to cross a total occlusion with a guidewire where, as a result, a separate intervention may be planned at a later date to cross the chronic total occlusion in order to provide the patient with a greater flow reserve. Peripheral procedures may involve extreme difficulty in positioning a guidewire at a distal location. It may be common for the interventionalist to have a set of tools available to assist in crossing these difficult-to-cross occlusions. Some physicians may commonly rely on a laser as an adjunct tool, while others may have a set of guidewires used for negotiating the occlusions. In either case, the mode of operation would be similar. The physician would determine that a particular occlusion needed an adjunct tool to help crossing; in this case, the forwardly directed fluid jet crossing catheter 10, the operation of which can be supported by the AngioJet® console or in the alternative, can be supported by combinations of other peripheral components. The forwardly directed fluid jet crossing catheter 10 can be combined with a pump in a sterile package using a sterile technique. The sterile pump would be loaded into the AngioJet® console and a supply of heparinized saline would be connected to the pump via a common bag spike and primed by stepping on a foot switch. The forwardly directed fluid jet crossing catheter 10 would be advanced to the treatment site by riding over the guidewire 120. The flexible tip 36 of the forwardly directed fluid jet crossing catheter 10 would be directed at the occlusion and the foot pedal depressed, thus providing a fluid jet stream of saline that would find the natural dissection plane and/or microchannels through the chronic total occlusion, whereby the guidewire 120 would be advanced. Then, the forwardly directed fluid jet crossing catheter 10 would be advanced and the process repeated until the occlusion was crossed. Once the occlusion was crossed, the intervention to treat the occlusion with either atherectomy or stenting could proceed. If the physician decided to use another guidewire, the physician could exchange the guidewire being used without loosing position and then introduce a new guidewire.

Various modifications can be made to the present invention without departing from the apparent scope thereof.

PARTS LIST 10 forwardly directed fluid jet crossing catheter
12 manifold
14 central body
16 hemostasis valve
18 high pressure connector
20 Luer fitting
22 Luer connector
24 Luer fitting
26 strain relief tube
28 proximal catheter tube (4 Fr)
30 low pressure cavity 32 distal catheter tube (3 Fr)
34 high pressure cavity
36 tapered tip
37 lumen
38 marker band
40 marker band
42 guidewire tube (polyimide)
44 lumen (of guidewire tube 42)
46 high pressure tube
48 lumen (of high pressure tube 46)
49 formable and shapeable catheter tip region
50 lumen (of proximal catheter tube 28)
52 lumen (of distal catheter tube 32)
54 adhesive plug seal
56 central passageway
56a small radius passageway section
56b large radius passageway section
58 cavity
60 cavity body
62 distal tubular body
64 annular connector flange
66 threads
68 threads
70 guidewire tubular adaptor
72 central bore
74 conical guide passageway
76 tapered bore
78 adhesive
80 injection hole
81 seal
82 passageway
84 boss
86 ferrule
88 passageway
90 passageway
92 proximal cavity
94 connector recess
96 tubular passageway
98 internal threads
100 threads
102 partially tapered passageway
104 passageway
106 high pressure branch passageway
108 manifold low pressure region
110 tapered transition
112 injection hole
114 entry hole
116 high pressure fluid
120 guidewire
122 fluid jet stream
122a fluid jet stream
124 vessel
126 chronic total occlusion
128 crossing It is claimed:

1. A forwardly directed fluid jet crossing catheter comprising:
   a manifold having a substantially straight tubular section and an off-line tubular section, said substantially straight tubular section having a proximal end and a distal end, said off-line tubular section being connected between said proximal and distal ends of said substantially straight tubular section;
   a flexible elongated catheter tube in communication with the substantially straight tubular section, the flexible elongated catheter tube having a proximal end and a distal end;
   a hollow tapered tip coupled to said distal end of said flexible elongated catheter tube, said hollow tapered tip having a proximal end and a distal end; and
   said flexible elongated catheter tube including therein:
      a plug seal near the distal end of the flexible elongated catheter tube, at least the plug seal and the hollow tapered tip forming a high pressure infusion cavity within the hollow tapered tip,
      an elongated guide wire tube extending from near said proximal end of said substantially straight tubular section, through said plug seal to said distal end of said hollow tapered tip, an opening of the elongated guide wire tube at the hollow tapered tip directed forward of the hollow tapered tip,
      an elongated high pressure tube extending from said off-line tubular section through said plug seal and emptying into the high pressure infusion cavity within the hollow tapered tip, and
      said elongated guide wire tube having a fluid entry hole in communication with the high pressure infusion cavity, wherein the high pressure tube is configured to deliver high pressure fluid into the high pressure infusion cavity, and from the high pressure infusion cavity to the elongate guide wire tube through the fluid entry hole, the high pressure fluid selectively and forwardly delivered by the opening of the elongated guide wire tube according to a position of a guide wire therein.

2. The forwardly directed fluid jet crossing catheter of claim 1, wherein said off-line tubular section is connected to said substantially straight tubular section at an acute angle.

3. The forwardly directed fluid jet crossing catheter of claim 1, wherein said flexible elongated catheter tube has an elongated proximal section and an elongated distal section between said distal end of said substantially straight tubular section of said manifold and said proximal end of said hollow tapered tip, and the internal plug seal is interposed between the proximal and distal sections of said flexible elongated catheter tube.

4. The forwardly directed fluid jet crossing catheter of claim 3, wherein said proximal end of said substantially straight section of said manifold has a hemo stasis valve attached thereto.

5. The forwardly directed fluid jet crossing catheter of claim 3, wherein said elongated guide wire tube and said elongated high pressure tube extend adjacent each other through a portion of said substantially straight tubular section and through said elongated proximal and distal sections of said flexible elongated catheter tube.

6. The forwardly directed fluid jet crossing catheter of claim 3, wherein said elongated proximal section of said flexible elongated catheter tube is a 4 french (4 f) catheter tube and said elongated distal section of said flexible elongated catheter tube is a 3 french (3 f) catheter tube.

7. The forwardly directed fluid jet crossing catheter of claim 1, wherein said distal end of said substantially straight tubular section of said manifold has a strain relief tube attached thereto and through which said flexible elongated catheter tube passes.

8. The forwardly directed fluid jet crossing catheter of claim 1, wherein said off-line tubular section of said manifold has a ferrule therein for securing said proximal end of said elongated high pressure tube.

9. The forwardly directed fluid jet crossing catheter of claim 1, wherein said substantially straight tubular section has an internal means for securing said proximal end of said guide wire tube therein.

10. The forwardly directed fluid jet crossing catheter of claim 9, wherein said internal means includes an adhesive located near said proximal end of said substantially straight tubular section of said manifold.

11. The forwardly directed fluid jet crossing catheter of claim 1, wherein said off-line tubular section of said manifold includes a tubular connector for passing a pressurized fluid into said proximal end of said high pressure tube.

12. The forwardly directed fluid jet crossing catheter of claim 11, wherein said tubular connector is threaded.

13. The forwardly directed fluid jet crossing catheter of claim 11, wherein said fluid is a saline solution or other suitable solution.

14. The forwardly directed fluid jet crossing catheter of claim 1, wherein said flexible elongated catheter tube is made from a braided polymer tubing.

15. The forwardly directed fluid jet crossing catheter of claim 1, wherein said elongated guide wire tube is made from a polyimide.

16. The forwardly directed fluid jet crossing catheter of claim 1, wherein said elongated high pressure tube is made from stainless steel.

17. The forwardly directed fluid jet crossing catheter of claim 1 comprising a guide wire within the elongated guide wire tube, the guide wire is slidable proximally and distally within the guide wire tube between tubular flow configuration and a solid flow configuration,
  in the tubular flow configuration the guide wire extends from the opening of the flexible guide wire tube and a flow of high pressure fluid from the high pressure infusion cavity generates a tubular jet of fluid having a first velocity from the opening and aligned along the guide wire, and
  in the solid flow configuration the guide wire is withdrawn from the opening of the flexible guide wire tube and the flow of high pressure fluid from the high pressure infusion cavity generates a solid jet of fluid having a second velocity from the opening, the second velocity greater than the first velocity.

18. The forwardly directed fluid jet crossing catheter of claim 17, wherein the guide wire in a plurality of positions between the tubular flow configuration and the solid flow configuration correspondingly varies the velocity of jets of fluid from the opening of the elongated guide wire tube between the first and second velocities.

19. The forwardly directed fluid jet crossing catheter of claim 1, wherein said elongated guide wire has a diameter of approximately 0.014 inch.

20. The forwardly directed fluid jet crossing catheter of claim 1, wherein said off-line tubular section is connected between a mid-section of said substantially straight tubular section and said proximal end of said substantially straight tubular section.

21. The forwardly directed fluid jet crossing catheter of claim 20, wherein said off-line tubular section is connected to said substantially straight tubular section at an acute angle, said acute angle being directed toward said proximal end of said substantially tubular section.

\* \* \* \* \*